(12) United States Patent
Zones et al.

(10) Patent No.: US 12,097,485 B2
(45) Date of Patent: *Sep. 24, 2024

(54) SMALL CRYSTAL SSZ-41, ITS SYNTHESIS AND USE

(71) Applicant: CHEVRON U.S.A. INC., San Ramon, CA (US)

(72) Inventors: Stacey Ian Zones, San Francisco, CA (US); Cong-Yan Chen, Kensington, CA (US)

(73) Assignee: CHEVRON U.S.A. INC., San Ramon, CA (US)

(*) Notice: Subject to any disclaimer, the term of this patent is extended or adjusted under 35 U.S.C. 154(b) by 171 days.

This patent is subject to a terminal disclaimer.

(21) Appl. No.: 18/064,336

(22) Filed: Dec. 12, 2022

(65) Prior Publication Data

US 2023/0131346 A1    Apr. 27, 2023

Related U.S. Application Data

(62) Division of application No. 17/693,503, filed on Mar. 14, 2022, now Pat. No. 11,547,986.

(60) Provisional application No. 63/160,979, filed on Mar. 15, 2021.

(51) Int. Cl.
*B01J 29/04* (2006.01)
*B01J 35/40* (2024.01)
*C01B 39/48* (2006.01)
*C07C 4/06* (2006.01)
*C07C 5/22* (2006.01)

(52) U.S. Cl.
CPC ............ *B01J 29/048* (2013.01); *B01J 35/40* (2024.01); *C01B 39/48* (2013.01); *C07C 4/06* (2013.01); *C07C 5/222* (2013.01); *B01J 2229/18* (2013.01); *C01P 2002/72* (2013.01); *C01P 2004/03* (2013.01); *C01P 2004/62* (2013.01); *C01P 2004/64* (2013.01); *C07C 2529/04* (2013.01)

(58) Field of Classification Search
CPC .... B01J 29/048; B01J 35/023; B01J 2229/18; C01B 39/06; C01B 39/48; C07C 4/06; C07C 2529/04; C01P 2002/72; C01P 2004/03; C01P 2004/62; C01P 2004/64; Y02P 30/20
See application file for complete search history.

(56) References Cited

U.S. PATENT DOCUMENTS

| | | | | |
|---|---|---|---|---|
| 4,703,025 A | * | 10/1987 | Kokotailo | C01B 33/2876 423/DIG. 23 |
| 10,167,200 B2 | * | 1/2019 | Zones | C07C 5/2724 |
| 11,674,092 B1 | * | 6/2023 | Otto | B01J 29/7869 585/752 |

* cited by examiner

*Primary Examiner* — In Suk C Bullock
*Assistant Examiner* — Jason Y Chong

(57) ABSTRACT

A method is disclosed for producing small crystal, high aluminum content zincoaluminosilicate crystalline materials having the SSZ-41 framework structure. The compositions made according to that method, as well as uses of the same, are also disclosed.

7 Claims, 5 Drawing Sheets

SMALL CRYSTAL SSZ-41, ITS SYNTHESIS AND USE

CROSS-REFERENCE TO RELATED APPLICATIONS

This application is a divisional application of U.S. patent application Ser. No. 17/693,503, filed Mar. 14, 2022, which claims priority to and the benefit of U.S. Provisional Patent Application No. 63/160,979, filed Mar. 15, 2021, the disclosures of which are incorporated herein by reference in their entirety.

FIELD

This disclosure relates to small crystal size SSZ-41 molecular sieve, its synthesis and its use as an adsorbent and a catalyst for organic conversion reactions.

BACKGROUND

Molecular sieves are a commercially important class of materials that have distinct crystal structures with defined pore structures that are shown by distinct X-ray diffraction (XRD) patterns and have specific chemical compositions. The crystal structure defines cavities and pores that are characteristic of the specific type of molecular sieve.

Crystalline molecular sieve SSZ-41, and its conventional preparation using a,w-di(N-methylpiperidine)polymethylene dicationic compounds and a,w-di(1,4-diazabicyclo[2.2.2]octane)polymethylene dicationic compounds as a structure directing agent, are taught by U.S. Pat. No. 5,591,421.

SSZ-41 materials are useful as catalysts in a variety of organic conversion reactions and, for such applications, it is found that activity and/or selectivity are generally improved when the molecular sieve product has a low silica-to-alumina molar ratio and a small crystal size. Unfortunately, however, aluminum can be a crystallization inhibitor with certain zeolites, including SSZ-41 materials, so that with most existing synthesis routes it is difficult to produce low silica-to-alumina molar ratio without significant production of impurity phases, particularly MTW framework type materials.

According to the present disclosure, it has been found that SSZ-41 can be produced at higher aluminum concentrations than previously exemplified. Moreover, the resultant product, composed of aggregates of small crystals of SSZ-41 with a low silica-to-alumina molar ratio is found to have improved activity and selectivity as an isomerization catalyst as compared to a catalyst prepared from conventional SSZ-41.

SUMMARY

In a first aspect, there is provided a zincoaluminosilicate molecular sieve having the framework structure of SSZ-41 and having a mean crystal size of 500 nm or less.

In a second aspect, there is provided a method of synthesizing a zincoaluminosilicate molecular sieve having the framework structure of SSZ-41, the method comprising: (1) forming a reaction mixture comprising: (a) a FAU framework type zeolite; (b) a source of zinc; (c) a structure directing agent (Q) comprising 1,1'-(1,4-butanediyl)bis[4-aza-1-azoniabicyclo[2.2.2]octane] dications; (d) a source of lithium; (e) a source of hydroxide ions; (f) water; and (g) seeds; and (2) subjecting the reaction mixture to crystallization conditions sufficient to form crystals of the zincoaluminosilicate molecular sieve; wherein the reaction mixture is free or essentially free of sodium.

In a third aspect, there is provided a process for converting a feedstock comprising an organic compound to a conversion product, the process comprising the steps of: (i) contacting the feedstock with a catalyst, at organic compound conversion conditions, to produce an effluent containing converted product, the catalyst comprising a zincoaluminosilicate molecular sieve having the framework structure of SSZ-41 and having a mean crystal size of 500 nm or less; and (ii) recovering converted product from the effluent.

DETAILED DESCRIPTION

Definitions

Figure 1:
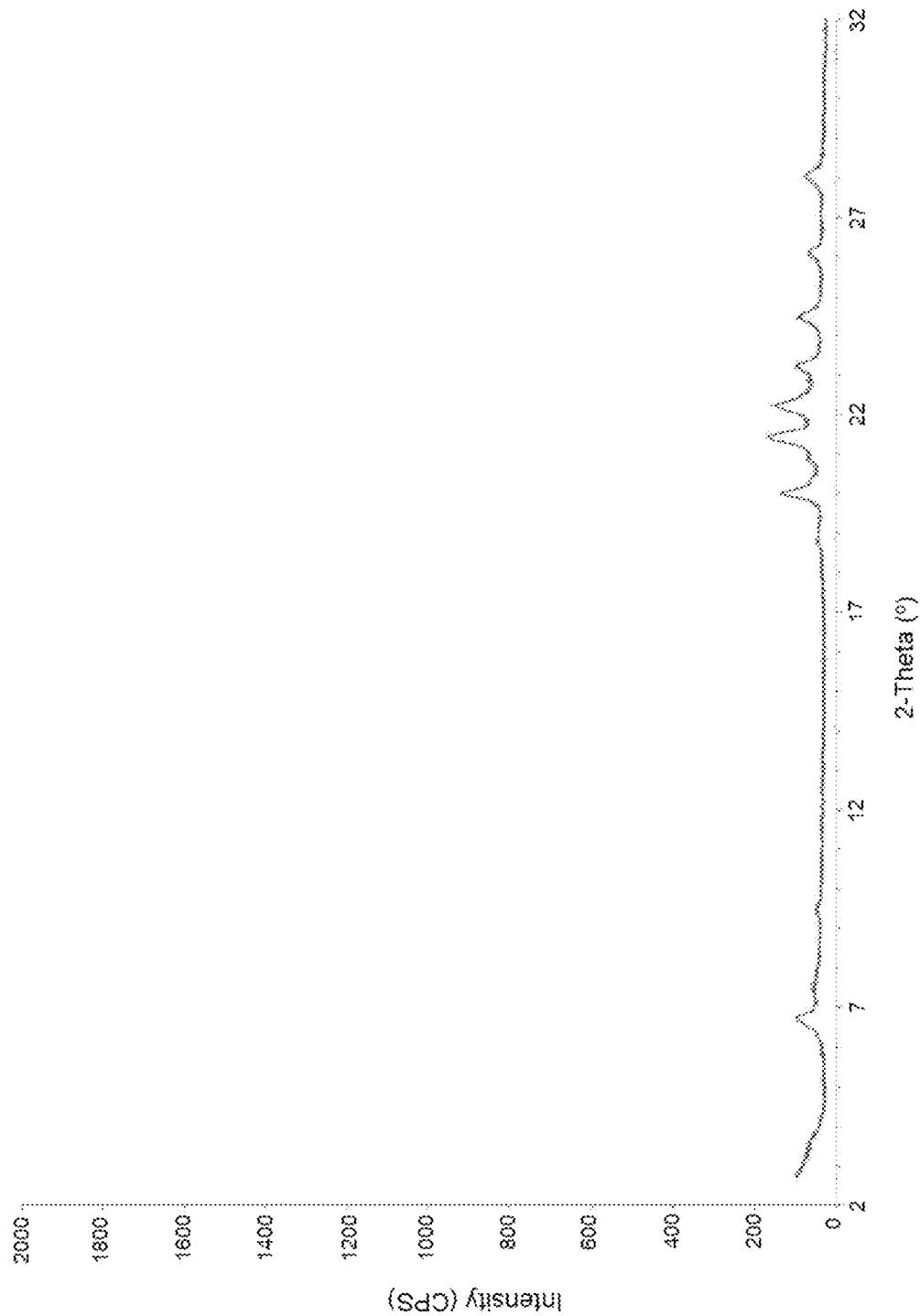
FIG. 1 shows a powder X-ray diffraction (XRD) pattern of as-synthesized product of Example 1.

As used herein, the term "zeolite" means an aluminosilicate molecular sieve having a framework constructed of alumina and silica (i.e., repeating $SiO_4$ and $AlO_4$ tetrahedral units).

The term "zincoaluminosilicate" refers to a molecular sieve having a framework constructed of zinc, alumina and silica (i.e., repeating $ZnO_4$, $AlO_4$ and $SiO_4$ tetrahedral units).

The term "framework type" as used herein has the meaning described in the "*Atlas of Zeolite Framework Types*" by Ch. Baerlocher, L. B. McCusker and D. H. Olson (Elsevier, Sixth Revised Edition, 2007).

The term "as-synthesized" refers to a molecular sieve in its form after crystallization, prior to removal of the structure directing agent.

The term "$SiO_2/Al_2O_3$ molar ratio" may be abbreviated as "SAR".

The term "SSZ-41x" refers to a zincoaluminosilicate molecular sieve having the structure of SSZ-41 and characterized as having a mean crystal size of 500 nm or less.

Synthesis of the Molecular Sieve

A zincoaluminosilicate molecular sieve having the framework structure of SSZ-41 can be synthesized by: (1) forming a reaction mixture comprising: (a) a FAU framework type zeolite; (b) a source of zinc; (c) a structure directing agent (Q) comprising 1,1'-(1,4-butanediyl)bis[4-aza-1-azoniabicyclo[2.2.2]octane] dications; (d) a source of lithium; (e) a source of hydroxide ions; (f) water; and (g) seeds; and (2) subjecting the reaction mixture to crystallization conditions sufficient to form crystals of the zincoaluminosilicate molecular sieve; wherein the reaction mixture is free or essentially free of sodium.

The reaction mixture can have a composition, in terms of molar ratios, within the ranges set forth in Table 1:

TABLE 1

| Reactants | Broadest | Secondary |
|---|---|---|
| $SiO_2/Al_2O_3$ | 30 to <100 | 50 to 90 |
| $SiO_2/ZnO$ | 15 to 75 | 20 to 40 |
| $Q/SiO_2$ | 0.10 to 0.50 | 0.15 to 0.40 |
| $Li/SiO_2$ | 0.05 to 0.35 | 0.10 to 0.30 |
| $OH/SiO_2$ | 0.10 to 0.50 | 0.15 to 0.40 |
| $H_2O/SiO_2$ | 10 to 60 | 15 to 45 | wherein Q comprises 1,1'-(1,4-butanediyl)bis[4-aza-1-azoniabicyclo[2.2.2]octane] dications.

The FAU framework type zeolite can be zeolite Y. The FAU framework zeolite can be an ammonium-form zeolite or a hydrogen-form zeolite (e.g., $NH_4^+$-form zeolite Y, $H^+$-form zeolite Y). The FAU framework type zeolite can have a $SiO_2/Al_2O_3$ molar ratio of at least 12 (e.g., 12 to 500, or 12 to 100, or 30 to 500, or 30 to 100, or 60 to 80). The FAU framework type zeolite can comprise two or more zeolites. Typically, the two or more zeolites are zeolites Y having different silica-to-alumina molar ratios. Examples of suitable aluminosilicate zeolites include Y zeolites CBV720, CBV760, and CBV780, available commercially from Zeolyst International, and Y zeolites HSZ-HUA385 and HSZ-HUA390, available commercially from Tosoh. The FAU framework type zeolite may be used as the sole or predominant source of silicon and aluminum in the reaction mixture.

The FAU framework type zeolite can be a zinc-exchanged zeolite (e.g., zinc-exchanged zeolite Y), wherein the zeolite can also be a zinc metal source of the reaction mixture. A "zinc-exchanged zeolite" refers to an aluminosilicate zeolite in which the zinc metal is disposed on the surface of and/or within the cages and/or pores of the aluminosilicate zeolite. It does not refer to aluminosilicates in which the zinc metal is in the aluminosilicate framework.

Additionally or alternatively, the source of zinc can be a zinc salt of an organic or inorganic acid. Representative zinc salts include zinc formate, zinc acetate, zinc citrate, zinc chloride, zinc bromide, zinc nitrate, and zinc sulfate.

Sources of lithium include lithium hydroxide and other lithium salts particularly lithium halides such as lithium chloride.

Preferably, the reaction mixture is free or essentially free of sodium. The term "essentially free" means that the indicated material is not deliberately added to the composition, or preferably not present at analytically detectable levels. It is meant to include compositions whereby the indicated material is present only as an impurity of one of the other materials deliberately added. For example, a composition that is "essentially free of sodium" may refer to a composition that contains no more than no more than 0.005%, no more than 0.002%, and/or no more than 0.001% sodium by weight. Applicants have found that the presence of sodium can lead to various impurities in final products. For example, when SSZ-41 is synthesized in the presence of sodium cations, ZSM-12 (MTW) can be an impurity in the final product.

The source of hydroxide ions can be lithium hydroxide. The structure directing agent can also be used to provide hydroxide ion.

The structure directing agent (Q) comprises a 1,1'-(1,4-butanediyl)bis-4-aza-1-azoniabicyclo[2.2.2]octane dication (DABCO-diquat-4) of the following structure (1):

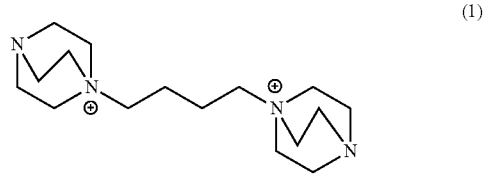 [SMILES: C(CC[N+]12CCN(CC1)CC2)C[N+]12CCN(CC1)CC2]

(1)

Suitable sources of Q are the hydroxides, chlorides, bromides, and/or other salts of the diquaternary ammonium compound.

The reaction mixture also contains seeds, typically SSZ-41 from a previous synthesis, desirably in an amount of from 0.1 to 20 wt. % by weight (e.g., 0.5 to 10 wt. %) relative to total weight of $SiO_2$ in the reaction mixture. Seeding can be advantageous to improve selectivity for SSZ-41x and/or to shorten the crystallization process.

It is noted that the reaction mixture components can be supplied by more than one source. Also, two or more reaction components can be provided by one source. The reaction mixture can be prepared either batchwise or continuously.

Crystallization of the desired molecular sieve from the above reaction mixture can be carried out under either static, tumbled or stirred conditions in a suitable reactor vessel, such as for example polypropylene jars or Teflon-lined or stainless-steel autoclaves, at a temperature of from 100° C. to 200° C. (e.g., 130° C. to 180° C.) for a time sufficient for crystallization to occur at the temperature used, such as from about 1 day to 14 days (e.g., 3 days to 10 days). Crystallization is usually conducted under pressure in an autoclave so that the reaction mixture is subject to autogenous pressure.

Once the desired molecular sieve crystals have formed, the solid product can be separated from the reaction mixture by standard mechanical separation techniques such as centrifugation or filtration. The recovered crystals are water-washed and then dried, for several seconds to a few minutes (e.g., 5 seconds to 10 minutes for flash drying) or several hours (e.g., 4 hours to 24 hours for oven drying at 75° C. to 150° C.), to obtain the as-synthesized molecular sieve crystals. The drying step can be performed under vacuum or at atmospheric pressure.

As a result of the crystallization process, the recovered crystalline molecular sieve product contains within its pores at least a portion of the structure directing agent used in the synthesis.

The as-synthesized molecular sieve may be subjected to thermal treatment, ozone treatment, or other treatment to remove part or all of the structure directing agent used in its synthesis. Removal of structure directing agent may be carried out using thermal treatment (e.g., calcination) in which the as-synthesized material is heated in an atmosphere selected from air, nitrogen, or a mixture thereof at a temperature sufficient to remove part or all of the structure directing agent. While sub-atmospheric pressure may be used for the thermal treatment, atmospheric pressure is desired for reasons of convenience. The thermal treatment may be performed at a temperature at least 370° C. (e.g., 400° C. to 700° C.) for at least a minute and generally not longer than 20 hours (e.g., 1 to 8 hours).

To the extent desired, any extra-framework metal cations (e.g., Li$^+$) in the molecular sieve can be replaced in accordance with techniques well known in the art by ion exchange with other cations. Replacing cations include metal ions, hydrogen ions, hydrogen precursor (e.g., ammonium ions), and mixtures thereof.

Characterization of the Molecular Sieve

In its as-synthesized and anhydrous form, the SSZ-41x molecular sieve can have a chemical composition, in terms of molar ratios, within the ranges set forth in Table 2:

TABLE 2

|  | Broadest | Secondary |
|---|---|---|
| SiO$_2$/Al$_2$O$_3$ | 30 to <100 | 50 to 90 |
| SiO$_2$/ZnO | 15 to 75 | 20 to 40 |
| Q/SiO$_2$ | >0 to 0.1 | >0 to 0.1 | wherein Q comprises 1,1'-(1,4-butanediyl)bis[4-aza-1-azoniabicyclo[2.2.2]octane] dications.

The crystals of the SSZ-41x molecular sieve can have a mean crystal size of 500 nm or less. Typically, the crystals can have a mean crystal size in a range of from 50 to 500 nm (e.g., 50 to 250 nm, or 75 to 500 nm, or 75 to 250 nm). Conventional forms of SSZ-41 typically have a mean crystal size of at least 1 micron.

The crystal size is based on individual crystals (including twinned crystals) but does not include agglomerations of crystals. Crystal size is the length of longest diagonal of the three-dimensional crystal. Direct measurement of the crystal size can be performed using microscopy methods, such as SEM and transmission electron microscopy (TEM). For example, measurement by SEM involves examining the morphology of materials at high magnifications (typically 1000× to 10,000×). The SEM method can be performed by distributing a representative portion of the molecular sieve powder on a suitable mount such that individual particles are reasonably evenly spread out across the field of view at 1000× to 10,000× magnification. From this population, a statistically significant sample of random individual crystals (e.g., 50 to 200) are examined and the longest diagonal of the individual crystals are measured and recorded. (Particles that are clearly large polycrystalline aggregates should not be included the measurements.) Based on these measurements, the arithmetic mean of the sample crystal sizes is calculated.

As conventionally synthesized, for example as taught by U.S. Pat. No. 5,591,421, molecular sieve SSZ-41 has a powder X-ray diffraction (XRD) pattern which, in the as-synthesized form of the molecular sieve, includes at least the peaks listed in Table 3 below and which, in the calcined form of the molecular sieve, includes at least the peaks listed in Table 4 below.

TABLE 3

Characteristic XRD Peaks for As-Synthesized SSZ-41

| 2-Theta [°] | d-Spacing [Å] | Relative Intensity [100 × I/Io] |
|---|---|---|
| 6.71 | 13.16 | S |
| 9.52 | 9.28 | W |
| 20.00 | 4.436 | VS |
| 21.40 | 4.149 | VS |
| 22.19 | 4.003 | S-VS |

TABLE 3-continued

Characteristic XRD Peaks for As-Synthesized SSZ-41

| 2-Theta [°] | d-Spacing [Å] | Relative Intensity [100 × I/Io] |
|---|---|---|
| 23.22 | 3.828 | S |
| 24.45 | 3.638 | S-VS |
| 26.07 | 3.415 | M-S |
| 28.01 | 3.183 | M |
| 35.52 | 2.525 | M |

TABLE 4

Characteristic XRD Peaks for Calcined SSZ-41

| 2-Theta [°] | d-Spacing [Å] | Relative Intensity [100 × I/Io] |
|---|---|---|
| 6.82 | 12.95 | VS |
| 9.64 | 9.17 | M-S |
| 20.14 | 4.41 | VS |
| 21.55 | 4.12 | S |
| 22.35 | 3.97 | M |
| 23.38 | 3.80 | M |
| 24.64 | 3.61 | M |
| 26.24 | 3.39 | M |
| 28.18 | 3.16 | M |
| 35.70 | 2.51 | W |

The X-ray diffraction data reported herein were collected by standard techniques using copper K-alpha radiation. The determination of the parameter 2-theta is subject to both human and mechanical error, which in combination can impose an uncertainty of about ±0.10° on each reported value of 2-theta. It is understood that the d-spacing values have a deviation determined based on the corresponding deviation ±0.10 degree 2-theta when converted to the corresponding values for d-spacing using Bragg's law. The relative intensities of the lines, I/Io, represents the ratio of the peak intensity to the intensity of the strongest line, above background. The relative intensities are given in terms of the symbols VS=very strong (>60), S=strong (≥40 and ≤60), M=medium (≥20 and <40), and W=weak (<20).

It is known that certain lines in the X-ray patterns of molecular sieves can tend to broaden as the relevant dimension of the molecular sieve crystal decreases, so that adjacent lines may begin to overlap and thereby appear as only partially resolved peaks or as unresolved broad peaks.

Applicants have discovered that the novel synthesis method described herein is capable of producing a high phase purity SSZ-41x molecular sieve, i.e., phase purities of 95% to more than 99%, as determined by Rietveld XRD analysis, for example. As used herein, the term "phase purity" with respect to a molecular sieve means the amount of a single crystalline phase of the molecular sieve (e.g., based on weight) relative to total weight of all phases (crystalline and amorphous) in the molecular sieve substance. Thus, while other crystalline phases may be present in the SSZ-41x molecular sieve, the SSZ-41x molecular sieve comprises at least 95% (e.g., at least 97%, or at least 98%, or at least 99%, or at least 99.9%) by weight SSZ-41x as a primary crystalline phase, wherein the weight percent SSZ-41x is provided relative to the total weight of the molecular sieve crystalline phases present in the composition. Examples of other crystalline phases which may be present as impurities can include undissolved faujasites (FAU) and/or MTW framework type materials.

INDUSTRIAL APPLICABILITY

The SSZ-41x materials described herein can be used as an adsorbent or as a catalyst to facilitate one or more of a wide variety of organic compound conversion processes. Examples of chemical conversion processes, which are effectively catalyzed by the SSZ-41x materials described herein, either alone or in combination with one or more other catalytically active substances (including other crystalline catalysts), include those requiring a catalyst with acid activity. Examples of organic conversion processes which may be catalyzed by the SSZ-41x materials described herein include cracking, hydrocracking, disproportionation, alkylation, oligomerization, and isomerization.

As in the case of many catalysts, it may be desirable to incorporate SSZ-41x materials with another material resistant to the temperatures and other conditions employed in organic conversion processes. Such materials include active and inactive materials and synthetic or naturally occurring zeolites as well as inorganic materials such as clays, silica and/or metal oxides such as alumina. The latter may be either naturally occurring, or in the form of gelatinous precipitates or gels, including mixtures of silica and metal oxides. Use of a material in conjunction with SSZ-41 (i.e., combined therewith or present during synthesis of the new crystal, which is active) tends to change the conversion and/or selectivity of the catalyst in certain organic conversion processes. Inactive materials suitably serve as diluents to control the amount of conversion in a given process so that products can be obtained in an economic and orderly manner without employing other means for controlling the rate of reaction. These materials may be incorporated into naturally occurring clays (e.g., bentonite and kaolin) to improve the crush strength of the catalyst under commercial operating conditions. These materials (i.e., clays, oxides, etc.) function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays which can be composited with SSZ-41x materials include the montmorillonite and kaolin family, which families include the sub-bentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with SSZ-41x also include inorganic oxides, such as silica, zirconia, titania, magnesia, beryllia, alumina, and any combination thereof.

In addition to the foregoing materials, SSZ-41x can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

The relative proportions of SSZ-41x and inorganic oxide matrix may vary widely, with the SSZ-41x content ranging from 1 to 90 wt. % (e.g., 2 to 80 wt. %) of the composite.

EXAMPLES

The following illustrative examples are intended to be non-limiting.

Example 1

A Teflon liner was charged with 0.036 g of anhydrous LiOH, 0.10 g of zinc acetate dihydrate, 0.44 g of Zeolyst CBV760 Y zeolite (SAR=60), 0.22 g of Tosoh 390HUA Y zeolite (SAR=500), seeds of as-synthesized SSZ-41 (based upon being 3% of the other the 2 FAU materials as silica sources), 3 mM of DABCO-diquat-4 dihydroxide, and water. The SDA solution and additional water totaled 5.6 g. All of the aluminum in the reaction mixture was provided by the 2 FAU materials. The liner was then capped, sealed inside a 23-mL autoclave, and heated at 150° C. under tumbling conditions (43 rpm) inside a convection oven for 6-8 days. The solids were then isolated by centrifugation, washed with deionized water, and dried in an oven at 95° C.

FIG. 1 shows the powder XRD of the as-synthesized product and is consistent with the product being SSZ-41x. The powder XRD pattern of the product appears to show broad features characteristic of materials with very small crystals.

Figure 2A:
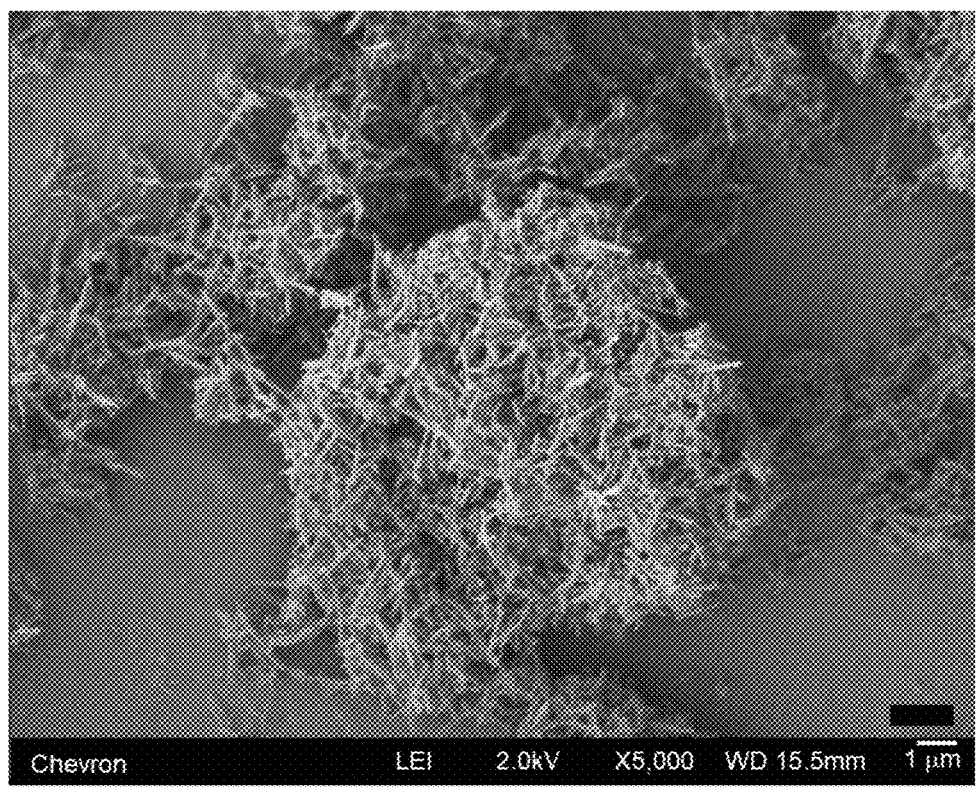
FIGS. 2A and 2B show Scanning Electron Micrograph (SEM) images of conventional SSZ-41 (large particle SSZ-41) and the as-synthesized SSZ-41x product of Example 1, respectively.
Figure 2B:
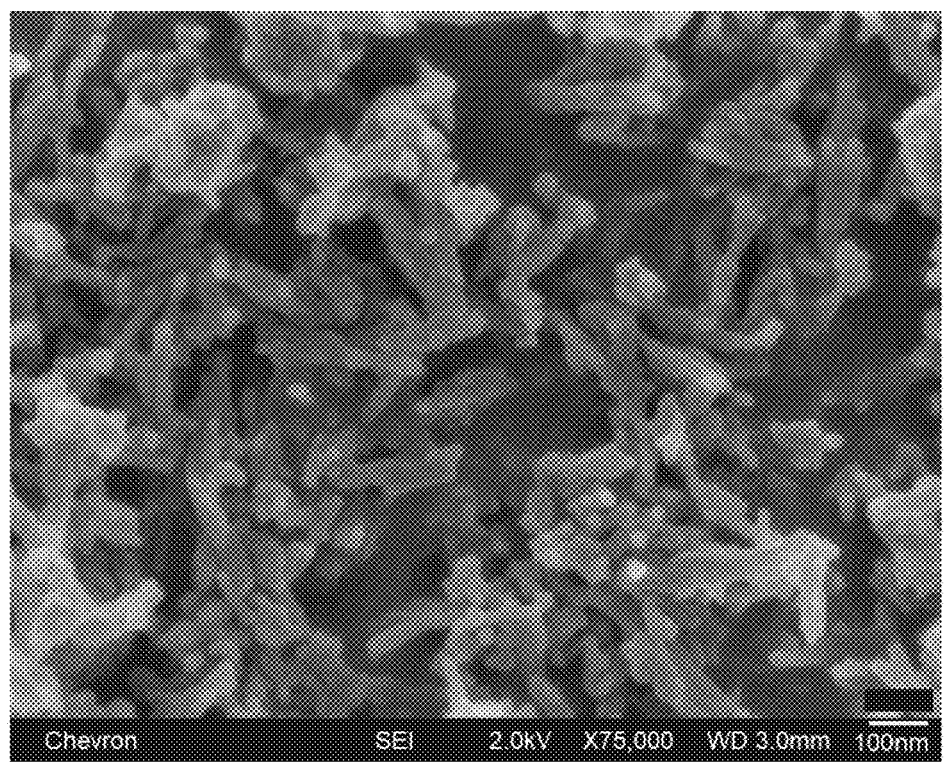

SEM images of conventional SSZ-41 (large particle SSZ-41) and the as-synthesized SSZ-41x product are shown in FIGS. 2A and 2B, respectively.

The as-synthesized product had an aluminum content of 1.04 wt. % (SAR=84), as determined by Inductively Coupled Plasma—Atomic Emission Spectroscopy (ICP-AES).

The as-synthesized material was then calcined in air by placing a thin bed of material in a calcination dish and heated in a muffle furnace from room temperature to 120° C. at a rate of 1° C./minute and held at 120° C. for 2 hours. Then, the temperature was ramped up to 540° C. at a rate of 1° C./min and held at 540° C. for 5 hours. The temperature was ramped up again at 1° C./minute to 595° C. and held 595° C. for 5 hours. The material was then allowed to cool to room temperature.

The calcined material was then converted to the ammonium form by heating in a solution of ammonium nitrate (typically, 1 g $NH_4NO_3$/1 g zeolite in 10 mL of $H_2O$ at 85° C. for at least 3 hours). The material was then filtered. This was repeated twice for a total of 3 exchanges. At the end, the material was washed with deionized water to a conductivity of less than 100 μS/cm dried in air at 85° C.

The acid site density was characterized using n-propylamine temperature-programmed desorption (TPD) and found to be 312.64 μmol $H^+$/g.

Analysis by nitrogen physisorption showed a t-plot micropore volume 0.1207 $cm^3$/g, a t-plot external surface area of 122.04 $m^2$/g, a BET surface area of 383.05 $m^2$/g, and a total pore volume of 0.933 $cm^3$/g.

Examples 2-5

For Examples 2-5 the starting materials outlined in Table 5 below were each charged to a Teflon liner. Zinc-exchanged CBV760 Y zeolite (SAR=60; Zeolyst) was prepared from the hydrogen form of the Y zeolite by ion exchange methods known in the art. The zinc-exchanged material had a zinc content of about 3 wt. %. The liner was then capped, sealed inside a 23-mL autoclave, and heated at 150° C. under tumbling conditions (43 rpm) inside a convection oven for 6-8 days. The solids were then isolated by centrifugation, washed with deionized water, and dried in an oven at 95° C. Recovered products were characterized by powder XRD.

TABLE 5

| | LiOH [g] | 1N NaOH [g] | Q [mM] | Zn/Y-zeolite[a] | Y-zeolite[b] | (CH$_3$CO$_2$)$_2$Zn [g] | H$_2$O [g] | SSZ-41 Seeds | XRD Result |
|---|---|---|---|---|---|---|---|---|---|
| Ex. 2 | 0.036 | — | 3 | 0.65 | — | — | 3 | 0.02 | SSZ-41x |
| Ex. 3 | — | 0.5 | 3 | 0.65 | — | — | 2.5 | 0.02 | MTW |
| Ex. 4 | 0.036 | — | 3 | 0.44 | 0.22 | 0.02 | 3 | 0.02 | SSZ-41x |
| Ex. 5 | — | 1.5 | 3 | 0.44 | 0.22 | 0.02 | 2.5 | 0.02 | SSZ-41x + MTW |

[a]Zinc-exchanged Zeolyst CBV-760 Y-zeolite (SAR = 60)
[b]Tosoh HUA390 Y-zeolite (SAR = 500)

Examples 6-16

For Examples 6-16 the starting materials outlined in Table 6 below were each charged to a Teflon liner. The zinc source was zinc acetate dihydrate. The liner was then capped, sealed inside a 23-mL autoclave, and heated at 150° C. under tumbling conditions (43 rpm) inside a convection oven for 6-8 days. The solids were then isolated by centrifugation, washed with deionized water, and dried in an oven at 95° C. Recovered products were characterized by powder XRD.

TABLE 6

| | LiOH [mM] | Q [mM] | Si Source | Si [mM] | Al Source | Al [mM] | Zn [mM] | H$_2$O [mL] | XRD Result |
|---|---|---|---|---|---|---|---|---|---|
| Ex. 6 | 2.5 | 5 | Precipitated silica | 16 | 60 SAR Y-zeolite | 0.3 | 0.77 | 7 | SSZ-41x + minor layered |
| Ex. 7 | 2.25 | 4.5 | Colloidal silica | 16 | Hydrated alumina | 0.3 | 0.68 | 7 | SSZ-41x + minor MTW |
| Ex. 8 | 2.5 | 5 | Precipitated silica | 16 | 30 SAR Y-zeolite | 0.27 | 0.77 | 11 | SSZ-41x |
| Ex. 9 | 2.5 | 5 | Precipitated silica | 16 | 12 SAR Y-zeolite | 0.30 | 0.77 | 11 | SSZ-41x |
| Ex. 10 | 1.5 | 3 | 500 SAR Y-zeolite | 9.5 | 60 SAR Y-zeolite | 0.22 | 0.34 | 5 | SSZ-41x |
| Ex. 11 | 1.5 | 3 | 500 SAR Y-zeolite | 9.5 | 60 SAR Y-zeolite | 0.22 | 0.22 | 5 | SSZ-41x |
| Ex. 12 | 1.9 | 5 | Precipitated silica | 16 | 12 SAR Y-zeolite | 0.30 | 0.77 | 11 | SSZ-41x and no impurity peaks near 12° 2θ |
| Ex. 13 | 1.25 | 5 | Precipitated silica | 16 | 12 SAR Y-zeolite | 0.30 | 0.77 | 11 | SSZ-41x with no impurities |
| Ex. 14 | 1.25 | 5 | 500 SAR Y-zeolite | 16 | 60 SAR Y-zeolite | 0.30 | 0.64 | 10 | SSZ-41x |
| Ex. 15 | 1.25 | 5 | 500 SAR Y-zeolite | 16 | 60 SAR Y-zeolite | 0.30 | 0.50 | 10 | SSZ-41 + MTW |
| Ex. 16 | 1.25 | 5 | 500 SAR Y-zeolite | 16 | 60 SAR Y-zeolite | 0.30 | 0.36 | 10 | SSZ-41 + MTW |

Example 17

Constraint Index

Constraint Index is a test to determine shape-selective catalytic behavior in zeolites. It compares the reaction rates for the cracking of n-hexane and its isomer 3-methylpentane under competitive conditions (see, e.g., V. J. Frillette et al., J. Catal. 1981, 67, 218-222).

Ammonium-exchanged SSZ-41x (NH$_4^+$/SSZ-41x) prepared according to Example 1 was pelletized at 4-5 kpsi and crushed and meshed to 20-40. Then, 0.47 g of this catalyst (dry weight as determined by TGA at 600° C.) was packed into a ⅜ inch stainless steel tube with catalytically inactive alundum on both sides of the zeolite bed. An ATS (Applied Test Systems, Inc.) furnace was used to heat the reactor tube. Helium was introduced into the reactor at 23 mL/min and atmospheric pressure. The catalyst was dehydrated at 482° C. for 2 hours. Then the reactor temperature was reduced to the pre-selected reaction temperature (e.g., 427° C. in this example). The helium flow rate was then adjusted to 9.4 mL/min and an equimolar mixture feed of n-hexane and 3-methylpentane was introduced into the reactor at a rate of 0.48 mL/h. The feed delivery was made via an ISCO pump. The on-line sampling of the product into a gas chromatograph (GC) began after 15 minutes of feed introduction. The Constraint Index value (including 2-methylpentane) was calculated from the GC data using methods known in the art. Representative results are shown in Table 7.

TABLE 7

Constraint Index Test Results

| Time [min] | Feed Conversion [%] | Constraint Index | Iso-C4/n-C4 |
|---|---|---|---|
| 15 | 56.3 | 1.09 | 3.36 |
| 45 | 36.8 | 0.84 | 3.61 |
| 75 | 30.6 | 0.72 | 3.68 |
| 105 | 28.5 | 0.75 | 3.9 |
| 135 | 24.7 | 0.72 | 3.83 |

The initial conversion with SSZ-41x prepared as described herein is more than 2 times greater than with conventional SSZ-41. Conventional SSZ-41, prepared according to U.S. Pat. No. 5,591,421, exhibited a conversion of 26% after 10 minutes.

Example 18

Catalyst Preparation

Ammonium-exchanged SSZ-41x (NH$_4^+$/SSZ-41x) prepared according to Example 1 was ion-exchanged in an aqueous palladium nitrate solution at a pH of about 10 and at a Pd loading of 0.5 wt. %. The Pd-exchanged zeolite was washed with deionized water to a conductivity of less than 50 mS/cm and dried. The zeolite was then calcined in air at 482° C. for 3 hours.

Example 19

Hydroconversion of n-Decane

For catalytic testing, the Pd catalyst of Example 18 was pelletized at 4-5 kpsi and crushed and meshed to 20-40. Then, 0.50 g of this catalyst (dry weight as determined by TGA at 600° C.) was packed in the center of a 23 inch-long×0.375 inch outside diameter stainless steel reactor tube loaded with catalytically inactive alundum on both sides of the zeolite bed. An ATS (Applied Test Systems, Inc.) furnace was used to heat the reactor tube. The catalyst was then pretreated in a down-flow hydrogen at a rate of 95 mL/min at atmospheric pressure with the following temperature program: from room temperature to 232° C. in 120 h, held at 232° C. for 1 h, from 232° C. to 316° C. in 1 h and held at 316° C. for 3.5 h, and then cooled down to 221° C. Then the reactor was pressurized to 1200 psig with a high hydrogen flow rate.

The reaction was started at 221° C., 1200 psig, 0.66 mL/h n-decane and 8.3 mL/min $H_2$ in the down-flow made. The feed delivery was made via an ISCO pump. The reaction temperature was stepwise by 5.6° C. up to 282° C. Products were analyzed by on-line capillary GC approximately once every sixty minutes. Raw data from the GC was collected by an automated data collection/processing system and hydrocarbon conversions were calculated from the raw data. Conversion is defined as the amount n-decane reacted in mol % to produce products other than the feed n-decane (i.e., iso-C10 and cracking products). The yield of iso-C10 is expressed as mole percent of feed n-decane converted to iso-C10 products. The yield of cracking products (smaller than C10) is expressed as mole percent of feed n-decane converted to cracking products.

Figure 3:
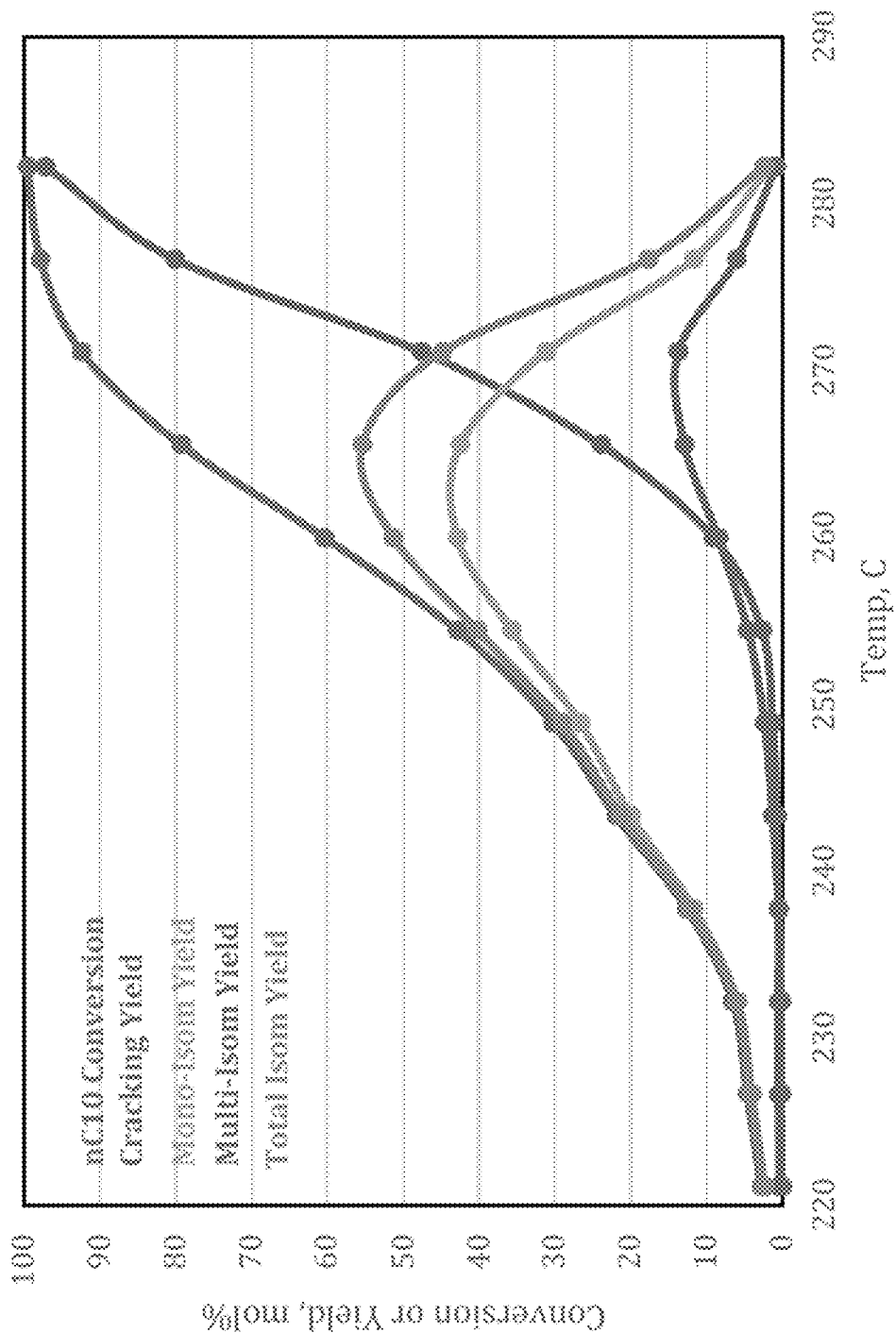
FIG. 3 is a plot of conversion or yield versus temperature for n-decane conversion over a Pd/SSZ-41x catalyst.
Figure 4:
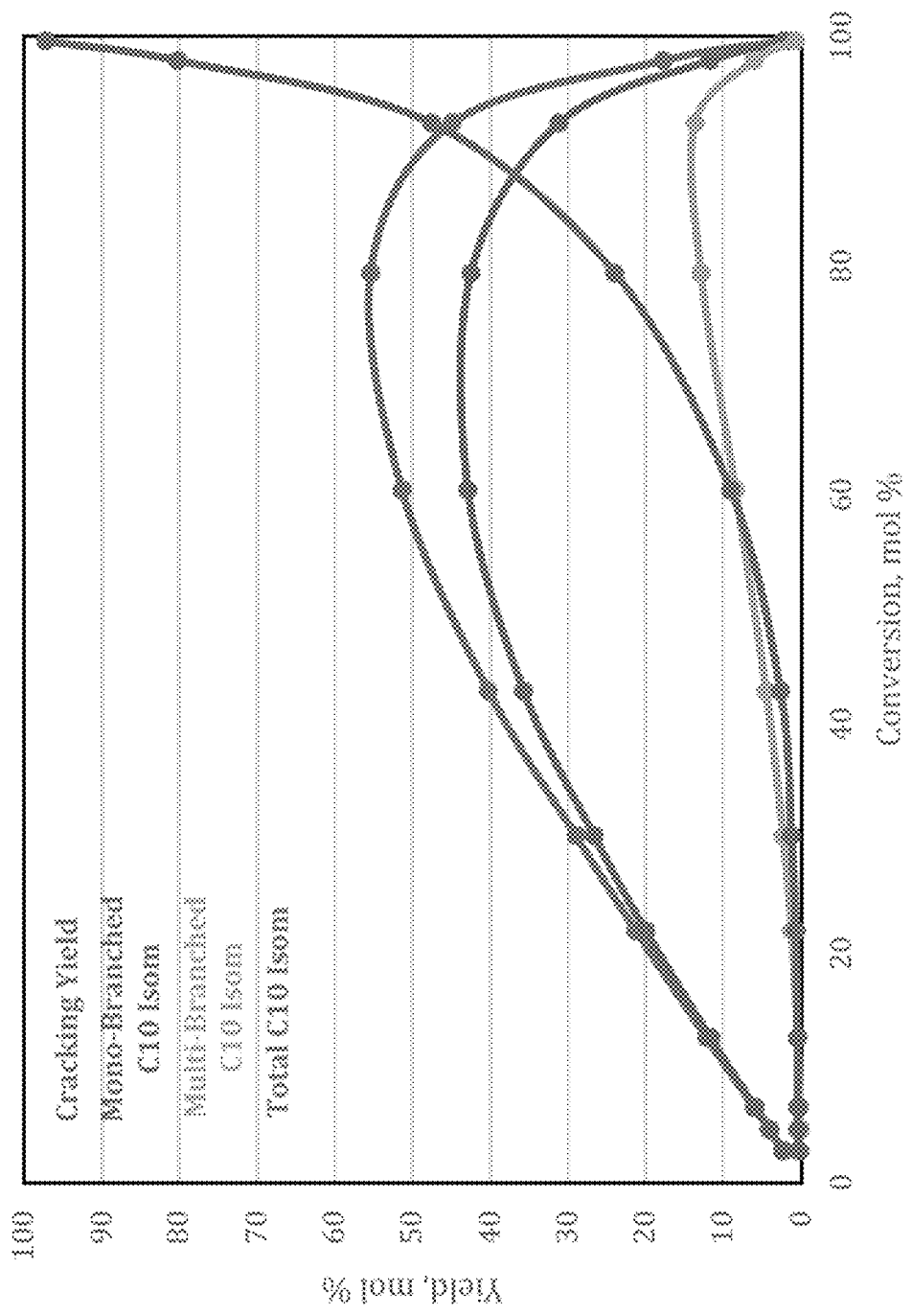
FIG. 4 is a plot of product yield versus conversion for n-decane conversion over a Pd/SSZ-41x catalyst.
Figure 5:
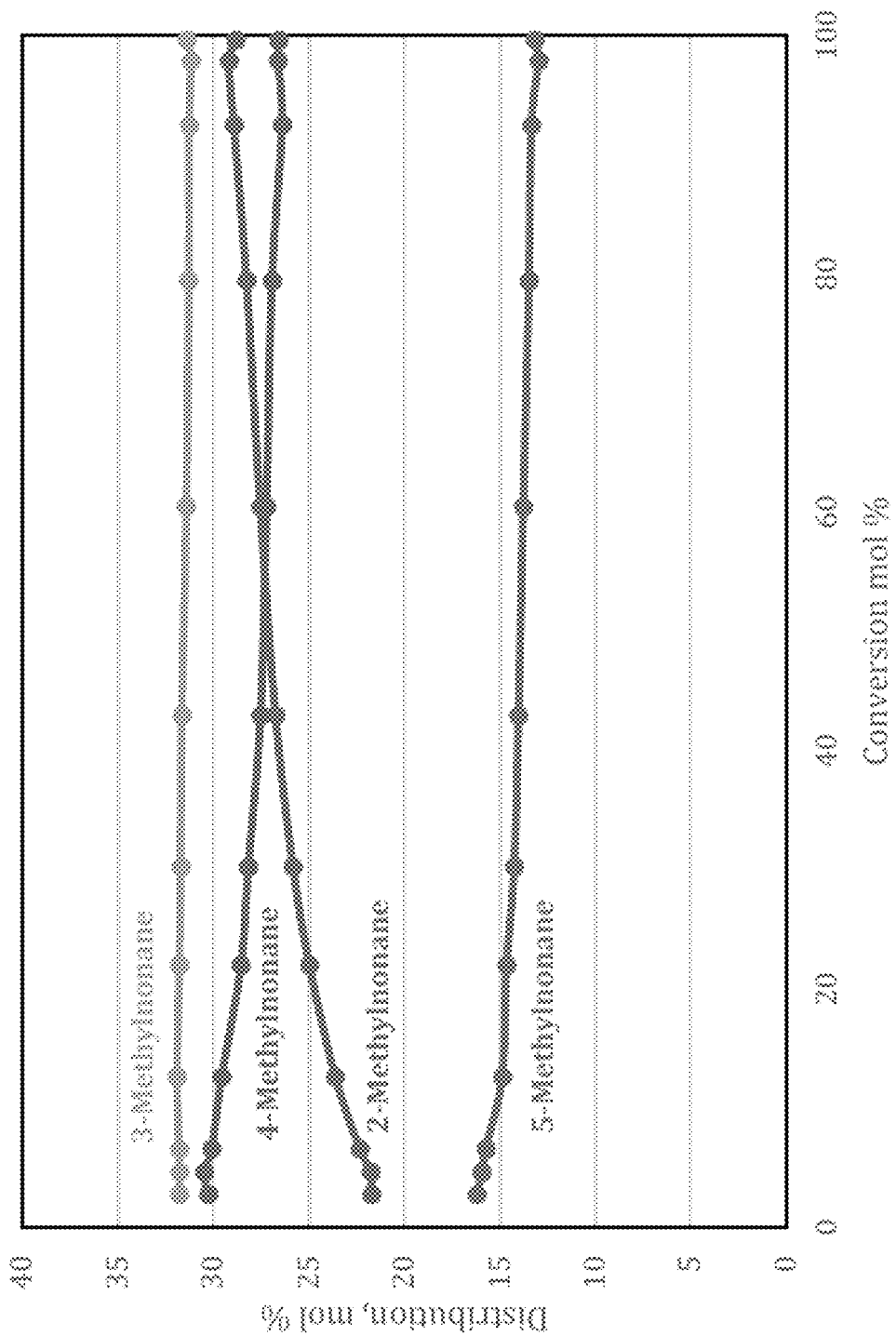
FIG. 5 is a plot of methylnonane isomer distribution versus conversion for n-decane conversion over a Pd/SSZ-41x catalyst.

The results of the hydrocarbon conversion are shown in FIGS. 3-5. As shown, the product, up to about 50% conversion, is more than 80% isomerized C10 and mostly the mono-branched C10 isomer. Moreover, an isomerization maximum was observed at about 260° C. which indicates a very active catalyst.

The invention claimed is:

1. A zincoaluminosilicate molecular sieve having the framework structure of SSZ-41 and having a mean crystal size of 500 nm or less, wherein the zincoaluminosilicate molecular sieve has a phase purity of at least 95% by weight.

2. The zincoaluminosilicate molecular sieve of claim 1, having a $SiO_2/Al_2O_3$ molar ratio in a range of from 30 to less than 100 and a $SiO_2/ZnO$ molar ratio in a range of from 15 to 75.

3. The zincoaluminosilicate molecular sieve of claim 1, wherein the mean crystal size is in a range of 50 nm to 500 nm.

4. The zincoaluminosilicate molecular sieve of claim 1, further comprising 1,1'-(1,4-butanediyl)bis[4-aza-1-azoniabicyclo[2.2.2]octane] dications in its pores.

5. The zincoaluminosilicate molecular sieve of claim 4, further comprising lithium as non-exchanged extra-framework cations.

6. A process for converting a feedstock comprising an organic compound to a conversion product, the process comprising the steps of:
   (i) contacting the feedstock with a catalyst, at organic compound conversion conditions, to produce an effluent containing converted product, the catalyst comprising the zincoaluminosilicate molecular sieve of claim 1; and
   (ii) recovering converted product from the effluent.

7. The process of claim 6, wherein the conversion process is at least one of a cracking process, a hydrocracking process, a disproportionation process, an alkylation process, an oligomerization process or an isomerization process.

\* \* \* \* \*